(12) United States Patent
Chen et al.

(10) Patent No.: US 11,365,411 B2
(45) Date of Patent: Jun. 21, 2022

(54) EFFICIENT RANDOM ACCESS TO DNA-ENCODED DATA

(71) Applicant: MICROSOFT TECHNOLOGY LICENSING, LLC, Redmond, WA (US)

(72) Inventors: Yuan-Jyue Chen, Seattle, WA (US); Bichlien Nguyen, Seattle, WA (US); Karin Strauss, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 124 days.

(21) Appl. No.: 16/748,774

(22) Filed: Jan. 21, 2020

(65) Prior Publication Data

US 2021/0222160 A1 Jul. 22, 2021

(51) Int. Cl.
 *C12N 15/10* (2006.01)
 *C12Q 1/6874* (2018.01)
(52) U.S. Cl.
 CPC ....... *C12N 15/1093* (2013.01); *C12Q 1/6874* (2013.01)
(58) Field of Classification Search
 None
 See application file for complete search history.

(56) References Cited

U.S. PATENT DOCUMENTS

| | | |
|---|---|---|
| 2015/0211048 A1 | 7/2015 | Ramsey et al. |
| 2019/0203281 A1 | 7/2019 | Robins et al. |
| 2019/0211374 A1 | 7/2019 | Makarov et al. |

FOREIGN PATENT DOCUMENTS

| | | |
|---|---|---|
| EP | 2875131 A1 | 5/2015 |
| WO | 2020005598 A1 | 1/2020 |

OTHER PUBLICATIONS

Laurie et al., "Simultaneous digital quantification and fluorescence-based size characterization of massively parallel sequencing libraries," BioTechniques 2013, 55:61-67. (Year: 2013).*

(Continued)

*Primary Examiner* — Kaijiang Zhang
(74) *Attorney, Agent, or Firm* — Benjamin A. Keim; Newport IP, LLC

(57) ABSTRACT

This disclosure provides techniques and systems for efficient random access to digital data encoded in oligonucleotides (e.g., DNA). Random access to DNA-encoded data is provided by amplification using polymerase chain reaction (PCR) and primer pairs that selectively amplify only the oligonucleotides encoding a desired set of digital data. Multiple separate random-access requests are prepared for multiplex DNA sequencing by generating copy-normalized amplification products. Copy-normalized amplification products are efficiently created by performing multiple singleplex PCR reactions in parallel and measuring the quantity of oligonucleotides in each reaction. The PCR reactions are performed in parallel through the use of multiple isolated reaction volumes such as water-in-oil microdroplets or individual wells on a plate. Copy normalization may be achieved by performing additional rounds of thermocycling on individual reaction volumes with low quantities of oligonucleotides or by batching samples with similar quantities of oligonucleotides together for multiplex DNA sequencing.

19 Claims, 4 Drawing Sheets

(56) References Cited

OTHER PUBLICATIONS

Andreadis, et al., "Use of Immobilized PCR Primers to Generate Covalently Immobilized DNAs for in Vitro Transcription/Translation Reactions", In Journal of Nucleic Acids Research, vol. 28, Issue 2, Jan. 15, 2000, 8 Pages.

Machado, et al., "Encapsulation of DNA in Macroscopic and Nanosized Calcium Alginate Gel Particles", Published in Langmuir, vol. 29, Issue 51, Nov. 27, 2013, pp. 15926-15935.

Organick, et al., "Random Access in Large-Scale DNA Data Storage", In Articles of Nature Biotechnology, vol. 36, Issue 3, Mar. 2018, 9 Pages.

Quan, et al., "dPCR: A Technology Review", Published in Sensors, vol. 18, Issue 4, Apr. 20, 2018, 27 Pages.

Takahashi, et al., "Demonstration of End-to-End Automation of DNA Data Storage", Published in Scientific Reports, vol. 9, Issue 1, Mar. 21, 2019, pp. 1-5.

Willsey, et al., "A Full-Stack Microfluidics Platform with Multi-Level Feedback Control", Retrieved from: https://pdfs.semanticscholar.org/824a/c476deba4f201b087a76b842f37c7cc9533e.pdf, 2018, 14 Pages.

Willsey, et al., "Puddle: A Dynamic, Error-Correcting, Full-Stack Microfluidics Platform", In Proceedings of the Twenty-Fourth International Conference on Architectural Support for Programming Languages and Operating Systems, Apr. 13, 2019, pp. 183-197.

Zhu, et al., "Single-Molecule Emulsion PCR in Microfluidic Droplets", In Journal of Analytical and Bioanalytical Chemistry, vol. 403, Issue 8, Jun. 1, 2012, pp. 2127-2143.

"Best Practices for Standard and Bead-Based Normalization in Nextera XT DNA Library Preparation Kits", Retrieved From: https://sapac.illumina.com/content/dam/illumina-marketing/documents/products/technotes/bead-based-normalization-tech-note-470-2016-007.pdf, Jan. 1, 2017, 4 Page.

Laurie, et al., "Simultaneous Digital Quantification and Fluorescence-Based Size Characterization of Massively Parallel Sequencing Libraries", In Journal of Biotechniques, vol. 55, Issue 2, Aug. 1, 2013, pp. 61-67.

"International Search Report and Written Opinion Issued in PCT Application No. PCT/US21/013502", dated Apr. 20, 2021, 15 Pages.

* cited by examiner

EFFICIENT RANDOM ACCESS TO DNA-ENCODED DATA

BACKGROUND

Oligonucleotides such as deoxyribonucleic acid (DNA) and ribonucleic acid (RNA) are now being used to store digital data. The digital data is encoded into a nucleotide sequence, synthesized, stored in an appropriate environment, extracted from storage, sequenced, and decoded back into digital data. Due to limits on the length of DNA strands that can be artificially synthesized, the nucleotides used to encode data for a single computer file are often split across a large number of DNA strands. Thus, the data store (e.g., a "DNA hard drive") may be a pool of many millions of DNA strands that encode the data of many thousands of computer files. The ability to selectively access specific data randomly rather than sequentially, referred to as "random access," is a desirable feature in a data storage system.

Without random access at a molecular level, accessing any data from a DNA data store could require sequencing the entire DNA pool and then performing random access using conventional digital computer techniques. For small DNA data stores this may be possible. However, as the scale of these systems increases, sequencing the entire DNA pool for every data request quickly becomes unworkable.

One technique for performing random access at the molecular level makes use of polymerase chain reaction (PCR) and specific primer pairs to selectively amplify portions of a DNA pool. With this technique, the DNA strands in the DNA pool have payload regions that encode digital data and the payload regions are flanked by primer binding sites. The DNA pool as a whole may be designed with a correspondence between the primer binding sites and encoded data. For example, all nucleotide sequences encoding data from the same computer file may be flanked by the same primer binding sites. Thus, the DNA encoding a specific computer file may be selectively amplified using a specific primer pair. The amplification product is sequenced and decoded thereby achieving random access.

However, random-access using PCR and specific primer pairs has inefficiencies and shortcomings that become more significant as the scale of DNA data storage systems increase. PCR and the subsequent sequencing of the amplification products are fundamentally biological processes that include variations and inconsistent behavior. Thus, random access based on selective PCR amplification, particularly when many random-access requests are combined, may waste reagents and time as well as generate unreliable sequence data leading to potential data loss. This disclosure is made with respect to these and other considerations.

SUMMARY

This disclosure provides methods and apparatus for efficient random-access to DNA-encoded data. The efficiencies and improvements provided by this disclosure relate to the steps of extracting DNA from storage and sequencing the DNA strands. A DNA data store may receive multiple random-access requests for specific data from one or more DNA pools. A random-access request such as for a specific computer file, for example, may be translated into a request to query a specific DNA pool using a specific primer pair. The translation may be performed by a digital computer that maintains a record of correspondence between digital data and molecular storage locations.

Processing these random-access requests in parallel (e.g., together in batch processes) is more efficient than processing each request separately. Selective PCR amplification of DNA sequences using specific primer pairs is performed by grouping multiple singleplex PCR reactions together. Multiple isolated reaction volumes each containing DNA strands from a DNA pool and multiple single-stranded oligonucleotides with the sequences of each member of a primer pair are sent through the same rounds of thermocycling. As used herein, "primer pair" refers to multiple molecules (e.g., many millions) of each of the two primers in a primer pair. Each of the isolated reaction volumes may contain DNA strands from a different DNA pool and/or a different primer pair. Thus, the amplification product of each may be different. This allows for the contents of each reaction volume to be independent of the other reaction volumes as in singleplex PCR, yet all of the reaction volumes are thermocycled together as in multiplex PCR.

The isolated reaction volumes may be microdroplets formed as water-in-oil emulsions. Microdroplets may also be formed by other techniques such as by encasing aqueous solutions in calcium alginate shells. Each microdroplet contains DNA from a DNA pool, a single primer pair, and PCR master mix. Multiple microdroplets may be placed in a thermocycler under conditions that allow PCR amplification to occur in the aqueous core of each microdroplet.

Wells on a plate may also be used to create isolated reaction volumes. All of the wells on a plate may be filled with the same solution of DNA from a DNA pool and PCR master mix. The variation across the individual reaction volumes is achieved by supplying different primer pairs to the wells. The primers can be supplied to each well on beads coated with single-stranded DNA that include the sequences of the primers. Each bead may be coated with the DNA sequences of both primers of a given primer pair. To prevent multiple different PCR reactions from occurring in the same well, the beads and wells may be sized so that only a single bead fits into a well. Thus, each well will include only a single primer pair. The surface of the plate may be coated with a thin layer of oil to prevent transfer between the wells. The entire plate may be sequentially heated and cooled so that the thermocycling necessary for PCR occurs in every well. In some implementations, the thermocycling may be spatially addressable so that each well can be subjected to a separate series of temperature changes.

Performing multiple PCR reactions in parallel makes the step of extracting DNA from a DNA pool more efficient but does not necessarily improve the efficiency of the subsequent sequencing. DNA sequencing can, like PCR, be performed on batches of molecules together. This is called multiplex sequencing. Multiplex sequencing is more efficient than sequencing each sample separately. However, the efficiency of multiplex sequencing can be increased further by controlling the quantity of DNA in the samples provided to a multiplex DNA sequencer.

Variations in the quantity of DNA in the samples analyzed in a single multiplex sequencing run may cause a multiplex DNA sequencer to perform unnecessary work when sequencing samples with higher quantities of DNA and fail to accurately sequence samples with lower quantities of DNA. This can be addressed through copy normalization—maintaining an approximately equal quantity of DNA across all of the samples sequenced together in the same sequencing run. Copy normalization may be necessary because of unequal PCR amplification. Due to differences in nucleotide sequences, different primer pairs can produce different amounts of amplification product even under identical PCR conditions. The quantity of DNA in each isolated reaction volume such as a microdroplet or well may vary due to differences in primer efficiency.

The quantity of DNA in the isolated reaction volumes can be measured to determine if, and to what extent, copy normalization is necessary. The quantity of DNA in a sample may be measured, for example, by adding a dye that fluoresces in proportion to the amount of DNA present. The amount of DNA in isolated reaction volumes with low levels of DNA (e.g., below a threshold level) may be increased by performing additional cycles of PCR. Microdroplets with low quantities of DNA may be routed back to a thermocycler for additional cycles of heating and cooling. Individual wells with low quantities of DNA may be subject to additional rounds of heating and cooling while other wells in the same plate are not.

Copy normalization of DNA quantity may also be performed by selectively grouping samples with approximately the same quantities of DNA into the same multiplex sequencing run. Microdroplets may be sorted into batches based on DNA quantity and all of the samples used in a single multiplex sequencing run may then be drawn from a batch of microdroplets with similar DNA quantities.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. Structures shown in the figures are representative and not necessarily to scale.

DETAILED DESCRIPTION

Figure 1:
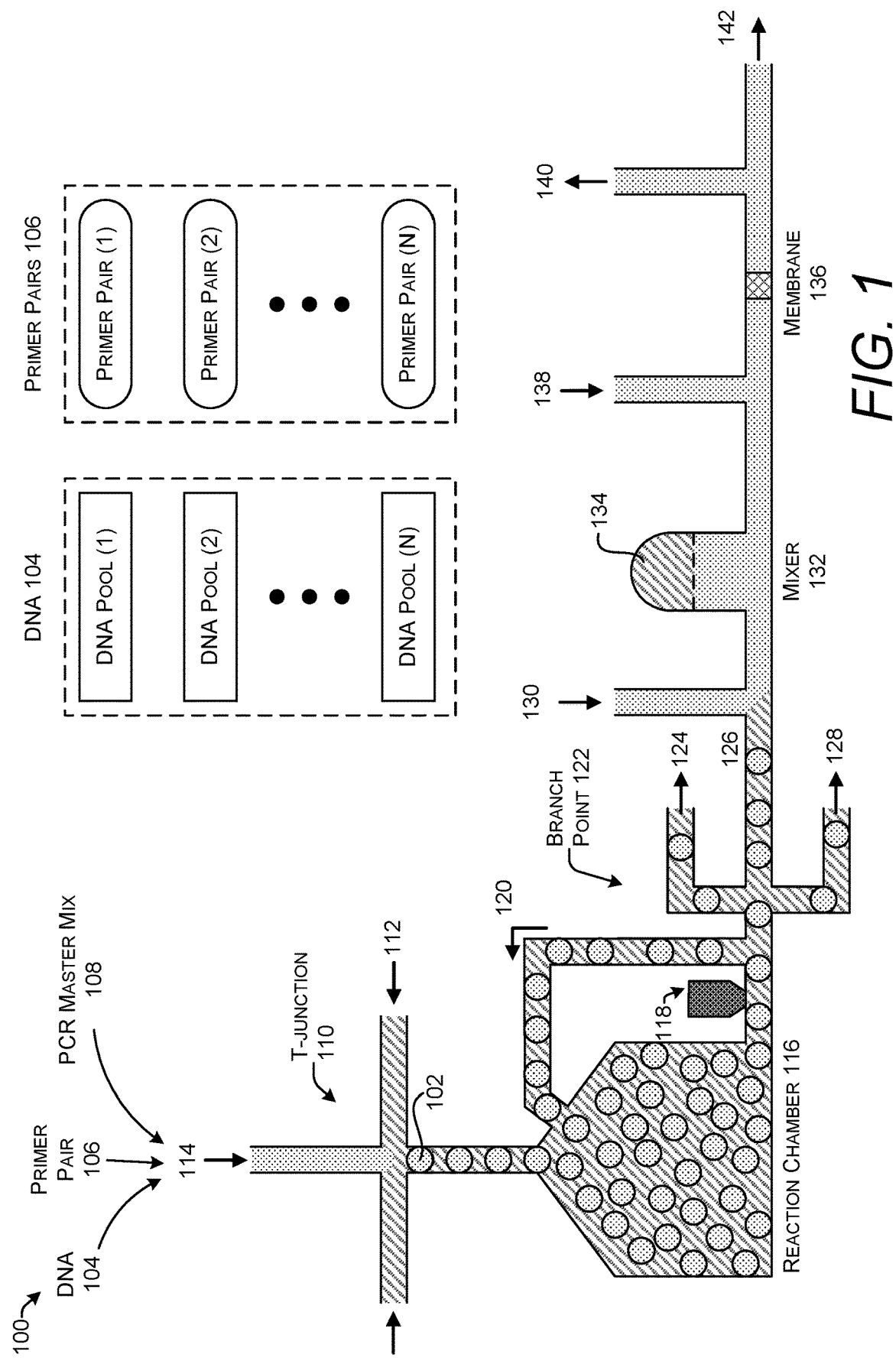
FIG. 1 is a diagram of an illustrative system for generating samples microdroplets containing DNA and a primer pair with processing that results in normalized DNA quantities for multiplex sequencing.

This disclosure provides techniques and systems for efficiently fulfilling random access requests sent to DNA data stores by generating samples of DNA with normalized DNA quantities for multiplex sequencing. Synthetic polynucleotides such as DNA may be used to store digital information by designing a sequence of nucleotide bases—adenine (A), cytosine (C), guanine (G), and thymine (T)—that encodes the zeros and ones of digital information. Advantages of using DNA rather than another storage media for storing binary data include information density and longevity. The sequence of nucleotide bases is designed on a computer and then DNA molecules with that sequence are generated by an oligonucleotide synthesizer. The DNA may be stored, selectively retrieved from storage, read by a DNA sequencer, and then decoded to retrieve the binary data.

Proof of concept systems and techniques for storing data in DNA have been previously demonstrated. See Lee Organick et al., *Random Access in Large-Scale DNA Data Storage*, 36:3 Nat. Biotech. 243 (2018) and Christopher N. Takahashi et al., *Demonstration of End-to-End Automation of DNA Data Storage*, 9 Sci. Rep. 4998 (2019). As DNA data storage systems increase in size and complexity the ability to efficiently respond to random-access requests will become increasingly important. Techniques for performing random-access using selective PCR amplification are described in Organick, supra and U.S. Pat. App. Publication No. 2018/0265921 entitled "Random Access of Data Encoded by Polynucleotides" and filed on Mar. 15, 2017.

Random access of digital data stored in DNA strands can be achieved using PCR to selectively amplify DNA that encodes the requested digital data. PCR amplification of DNA increases by several orders of magnitude the number of copies of the target DNA sequences. Selective amplification increases the number of copies of the DNA strands encoding the desired digital data much more than other DNA strands in the same pool. For example, DNA strands encoding digital data for two or more different data files can be stored together in the same container: a DNA pool. Request for the digital data corresponding to just one of those files, a random-access request, begins with obtaining the sequence of DNA strands encoding the selected digital data without sequencing all the DNA strands in the DNA pool.

Selective amplification through PCR increases the number of DNA strands encoding the desired digital data by many orders of magnitude relative to other DNA strands in the same DNA pool. The amplification product can be sequenced by a DNA sequencer and the reads produced from sequencing are then decoded to reproduce the original bits of the requested digital data. Although the other DNA strands from the DNA pool are still present in the amplification products, the probability of sequencing these DNA strands is low because there are so many fewer copies. Thus, selective amplification provides specification through dilution.

The correlation between primer pairs and digital data may be implemented by assigning a unique group identifier to each DNA strand that contains data for a particular data file. The individual group identifier may be encoded as a specific sequence of nucleotides in the DNA strands. In some implementations, this group identifier may be a primer binding site. With this design, DNA that amplifies using a primer that hybridizes to the primer binding site will be DNA that encodes digital data from that particular data file. In this way, the DNA strands that encode the digital data being requested can be selectively amplified and subsequently sequenced and decoded to provide the requested digital data.

PCR amplification can be used to selectively "pullout" specific sequences of DNA from a DNA pool. Different primer pairs are used to respond to requests for different sets of data. As the scale of a DNA storage system grows, there will likely be a very large number of different primer pairs used. Different primer pairs inherently have different sequences which can result in uneven amplification. However, PCR performed with different primer pairs may generate different quantities of DNA even if all other variables are constant. This is likely due to variation in primer binding strength, non-specific binding, primer-dimer formation, and other factors. Thus, without copy-normalization, otherwise similar random-access requests can generate different amounts of amplified DNA.

One subcategory of microfluidics is droplet-based microfluidics which creates discrete volumes with the use of immiscible phases. The ultrahigh-throughput generation of uniform droplets with nL to pL volume greatly enhances the capability of microfluidics to perform a large number of reactions without increasing device size or complexity. Microfluidic droplet technology has the advantages of compartmentalizing reactions into discrete volumes, performing highly parallel reactions in monodisperse droplets, reducing cross-contamination between microdroplets, eliminating PCR bias and nonspecific amplification, as well as enabling fast amplification with rapid thermocycling.

Copy-normalization sequencing is the process of equalizing the quantity of DNA in samples for a multiplex sequencing run in which multiple DNA samples that contain or should contain the same sequence of nucleotides are sequenced. In next-generation sequencing (NGS) multiplexing is performed by loading multiple—often thousands—of separate samples on a single flow cell. This increases the efficiency of NGS and reduces costs. But uneven quantities of DNA from different random-access requests when combined in the same flow cell can lead to inconsistencies in quality of the sequence data output by the DNA sequencer. Variations in DNA quantity for samples placed in different flow cells do not cause these deficiencies.

Samples with high quantities of DNA are likely to be overrepresented on a flow cell while those with low quantities are likely underrepresented. Overrepresentation may not affect accuracy because it increases read depth. However, this wastes capacity and leads to inefficient use of multiplex DNA sequencing machines and consumes additional reagents which increases costs. Underrepresentation might result in poor read depth and unreliable sequence data, wasting capacity and potentially making it impossible to accurately decode the sequence into the original binary data. Therefore, normalizing DNA quantities or DNA copy number prior to sequencing improves the accuracy and efficiency of multiplex sequencing which improves the accuracy and efficiency of random-access requests for DNA-encoded data. Identical quantities of DNA across samples not required, but the extent of variation in DNA quantities between samples should be minimized.

In this disclosure, oligonucleotides, which are also referred to as polynucleotides, include both DNA, RNA, and hybrids containing mixtures of DNA and RNA. DNA includes nucleotides with one of the four natural bases cytosine (C), guanine (G), adenine (A), or thymine (T) as well as unnatural bases, noncanonical bases, and/or modified bases. RNA includes nucleotides with one of the four natural bases cytosine, guanine, adenine, or uracil (U) as well as unnatural bases, noncanonical bases, and/or modified bases. Nucleotides include both deoxyribonucleotides and ribonucleotides covalently linked to one or more phosphate groups. Although DNA may be referred to specifically as an illustrative oligonucleotide this is not limiting and it is to be understood that other oligonucleotides may be used instead of DNA.

Detail of procedures and techniques not explicitly described in this or other processes disclosed of this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual*, Cold Spring Harbor Laboratory Press, 4$^{th}$ ed. (2012).

FIG. 1 shows a first illustrative random-access system 100 for generating microdroplets 102 with samples of DNA 104 and primer pairs 106 that have normalized DNA quantities. The random-access system 100 creates a large number of microdroplets 102 that can each contain a unique combination of DNA 104 and a primer pair 106 together with the other reagents necessary for PCR in a PCR master mix 108. Each of the microdroplets 102 provides an isolated reaction volume that prevents interaction between the components in separate microdroplets 102. This dramatically reduces hardware complexity of the system 100 and allows for a much higher density of separate reactions as well as for easier automated manipulation than other techniques for singleplex PCR such as multiple flip-top tubes in a conventional thermocycler.

The microdroplets 102 may be created by forming an emulsion of oil and water. The water-in-oil microdroplets 102 may be created with a T-junction 110. T-junction 110 geometries contain a continuous phase main channel 112 and a disperse phase inlet channel 114, perpendicular to each other, which looks like the two branches of the "T." A droplet formation cycle starts with the stream of the disperse phase (aqueous DNA-containing PCR solution) penetrating into the main channel (an immiscible oil such as mineral oil), and a microdroplet 102 begins to grow. The pressure gradient, the shear force, and the interfacial tension at the fluid-fluid interface distort and elongate the microdroplet 102 in the downstream direction, until the neck of the disperse phase becomes thin and eventually breaks. This releases the microdroplet 102 downstream into the main channel 112. Then the tip of the disperse phase retracts to the end of inlet and the process repeats. Empirically, the size of microdroplet 102 and its generation process are highly dependent on the capillary number, the flow rates, the viscosity ratio, and the channel geometry. See Zhi Zhu et al., *Single-molecule emulsion PCR in microfluidic droplets*, 403 Anal. Bioanal. Chem. 2127 (2012).

The microdroplets 102 may alternatively be created by encapsulation of an aqueous solution in a membrane. The membrane may be formed from a material such as calcium alginate. Calcium alginate (calcium β-D-mannopyranuronosyl-(1→4)-α-L-gulopyranuronosyl-(1→4)-α-L-gulopyranuronate) is a water-insoluble, gelatinous, cream-colored substance that can be created through the addition of aqueous calcium chloride to aqueous sodium alginate. An aqueous solution containing the DNA 104, primer pair 106, and PCR master mix 108 may be provided through the inlet channel 114 while the calcium alginate is provided through the main channel of the T-junction 110. Calcium alginate forms shells around water or aqueous solutions. The calcium alginate shells themselves may be suspended in an alcohol solution which prevents evaporation of water and reduces the adhesion of the shells to each other. Techniques for encapsulating DNA in calcium alginate shells are described in Alexandra H. E. Machado et al., *Encapsulation of DNA in Macroscopic and Nanosized Calcium Alginate Gel Particles*, 29 Langmuir 15926 (2013).

In an implementation, the microdroplets 102 may also be nested microdroplets that include two or more layers of encapsulation surrounding an aqueous core that holds the DNA 104. For example, calcium alginate spheres may be placed into a water-in-oil emulsion creating two layers of isolation between reaction volumes. Each reaction volume containing DNA 104, a primer pair 106, and PCR master mix 108 is encapsulated within a calcium alginate shell which itself is within a water droplet surrounded by oil.

Varying the inputs into the inlet channel 114 controls the contents of the microdroplets 102. Each microdroplet 102 may represent a response to a different random-access request. The DNA 104 is obtained from one of one or more DNA pools. Each DNA pool is a separate container holding many thousands, millions, or more individual DNA strands that encode digital data. DNA from one of the DNA pools is converted to an aqueous solution, if not in that form already, and a small portion is removed and used as the DNA 104 introduced into the inlet channel 114.

The primer pair 106 may be obtained from a collection of pre-synthesized primer pairs. The sequences of the primer pairs that could potentially be used to amplify DNA fragments from one of the DNA pools may be known based on the design of the DNA strands use for encoding digital data. For example, for a first DNA Pool may contain DNA strands that have primer binding sites corresponding to one of 50 different primer pairs. The primer pair 106 may also be synthesized on-demand using an oligonucleotide synthesizer or other techniques for synthesis of short single-stranded polynucleotides. The same primer pair 106 may be used with different DNA pools to fulfill different random-access requests. For example, primer pair (2) may be used to amplify DNA corresponding to a first file from DNA pool (1) while the same primer pair (2) would be used to amplify DNA corresponding to a second file if combined with the DNA of DNA pool (2).

The PCR master mix 108 includes a DNA polymerase, deoxyribonucleotide triphosphates (dNTPs), in a reaction buffer. Techniques for selection and creation of suitable PCR master mixes are known to those of ordinary skill in the art. Many suitable master mixes are also commercially available such as, for example, the Gibson Assembly® master mix available from New England BioLabs, Inc.

The DNA 104 from a DNA pool, the primer pair 106, and the PCR master mix 108 may be mixed by any automated or manual technique such as pipetting, microfluidics, laboratory robotics, etc. One automated system that may be used for mixing these, or other reagent discussed elsewhere in this disclosure, is a digital microfluidics device such as the "PurpleDrop" device described in Max Willsey et al., *Puddle: A Dynamic, Error-Correcting, Full-Stack Microfluidics Platform*, ASPLOS'19 Apr. 13-17, 2019 and Max Willsey et al., *A Full-Stack Microfluidics Platform with Multi-Level Feedback Control*, (2018).

The T-junction 110 is connected to a reaction chamber 116. The reaction chamber 116 the temperature-controlled chamber such as a chamber of a thermocycler. The temperature in the reaction chamber 116 can be precisely controlled to thermocycle the microdroplet 102 under conditions that will result in PCR amplification. Specific temperatures and timings for PCR reactions are known to those of ordinary skill in the art and may be performed using any conventional protocol. For example, one protocol is (1) 95° C. for 3 min, (2) 98° C. for 20 s, (3) 62° C. for 20 s, (4) 72° C. for 15 s, (5) go to step 2 a varying number of times, and (6) 72° C. for 30 s.

Thus, during thermocycling a different PCR reaction may occur in each microdroplet 102. That is, each microdroplet 102 may contain a unique combination of DNA 104 and primer pair 106. However, it is also possible that multiple microdroplets 102 may contain the same combination of DNA 104 and primer pair 106. Because the DNA 104 may be taken from any one of a number of different DNA pools, the use of microdroplets 102 to create isolated reaction volumes allows for amplification of DNA from a mix of different DNA pools in the same reaction chamber 116. Mixing multiple DNA pools while maintaining specificity of amplification products may not be possible in conventional multiplex PCR because the primer pairs 106 would have access to DNA strands from all of the multiple DNA pools. The reaction chamber 116 may hold many thousands or tens of thousands of microdroplets 102.

The system 100 may also include a sensor 118 that detects DNA concentrations in individual microdroplets 102. The sensor 118 may be positioned on a portion of the system 100 such as narrow tube in which single microdroplets 102 pass before the sensor 118. The sensor 118 may be implemented as an ultraviolet (UV) light and corresponding UV photosensor to measure DNA quantity by the amount of UV absorption The sensor 118 may be implemented as a laser and fluorescence detector that excite and detect fluorescence emitted from a DNA-binding dye such as an intercalating dye. Examples of fluorescent dyes that may be used for detecting DNA include EvaGreen® available from Biotium, PicoGreen, and SYBR Green. The DNA binding dye may be included in the PCR master mix 108 or separately added to the inlet channel 114. The sensor 118 may be adapted from devices described in Phenix-Lan Quan et al., *dPCR: A Technology Review*, 18(4) Sensors (Basel) 1271 (2018).

In an implementation, sensing could be performed in the reaction chamber 116 by configuring the reaction chamber 116 to include a plate with multiple wells each sized to hold a single microdroplet 102. For example, the plate may be created using techniques for fabricating semiconductors in order to create wells with the dimensions that hold only a single microdroplet 102. The plate may contain individually addressable heating elements under each well. The heating elements (coupled with a system for cooling all or part of the plate) may provide the temperature cycling used for PCR. Thus, PCR amplification is performed for the DNA in each microdroplet in its respective well. The microdroplets 102 may contain a fluorescent dye that is used as described above to monitor the quantity of DNA in each well. Normalization of DNA quantities are achieved by selectively providing additional cycles of PCR to those wells with DNA quantities that are below a threshold level. This can normalize the quantity of DNA in each well 204. Thus, one or more sensors 118 may be configured to detect fluorescence levels in the wells as PCR is being performed. Examples of suitable plates and aspects of this technique for DNA quantity normalization are discussed below in the section describing FIG. 3.

Measurement of DNA quantities in individual microdroplet 102 makes it possible to process the microdroplet 102 differentially based on DNA quantity. Individual microdroplets 102 may be routed through different pathways within the system 100 based on DNA quantity using microfluidics and/or cell-sorting techniques such as electrostatic sorting.

A return pathway 120 may return microdroplet 102 with low levels of DNA (e.g., levels of DNA below a specified threshold) to the reaction chamber 116 or to a separate reaction chamber (not shown) for additional cycles of PCR amplification. Providing the microdroplet 102 with additional heating and cooling cycles will further increase the quantity of DNA produced by PCR amplification.

A branch point 122 may be used to sort the microdroplets 102 into two or more different batches based on DNA quantity. For example, the microdroplets 102 may be sorted into batches of high, medium, and low DNA quantities and routed to different pathways 124, 126, and 128 respectively.

However, the microdroplets 102 may be divided into more than three different batches. The cutoff thresholds of DNA quantities for placing a given microdroplet 102 in a DNA quantity-sorted batch may be derived from real-time DNA quantities measured by the sensor 118 or from previously collected data. The remainder of pathways 124 and 128 (not shown) may be the same as pathway 126.

In some implementations, both the return pathway 120 and the branch point 122 may be used together. For example, the return pathway 120 may be an additional pathway off of the branch point 122 and microdroplets 102 with DNA quantities that are below a threshold level may be routed to the return pathway 120 for further PCR amplification. For example, the branch point 122 may separate the microdroplets 102 into groups of high, medium, low, and very low DNA quantities with the microdroplets 102 having very low DNA quantities being routed to the return pathway 120.

After additional rounds of PCR or batching based on DNA quantity, the microdroplets 102 moving beyond the branch point 122 (e.g., through pathway 126) will have normalized quantities of DNA. The DNA quantities will not necessarily be identical in every microdroplet 102 at this point but the variation in DNA quantities will be much less than in the microdroplets 102 inside the reaction chamber 116.

Prior to DNA sequencing the oil is separated from the amplified DNA products. The emulsion may be broken by adding an alcohol such as 2-butanol through inlet 130 prior to mixing with a mixer 132. The mixer 132 may be any type of mixer suitable for mixing liquids without shearing DNA strands such as a magnetic stirrer or a vortex mixer. Mixing the emulsion and alcohol causes an organic phase 134 that contains the oil. The organic phase 134 may be discarded or processed and reused.

For microdroplets 102 formed with calcium alginate, the amplified DNA is released from the microdroplets 102 by mechanically disrupting the calcium alginate shells. Disruption may be performed by using microneedles, magnetic beads, or sonification. Alternatively, heating the microdroplets 102 to about 150° C. may also disrupt the calcium alginate shells. After the microdroplets 102 are broken, the remains of the calcium alginate shells are still present in an aqueous solution that contains the amplified DNA products.

The resulting aqueous phase contains the amplified DNA from the microdroplets 102. The DNA corresponding to different random-access requests is no longer physically separated by the microdroplets 102. Prior to sequencing the DNA is cleaned. The DNA may be adsorbed on a membrane 136 such as a silica or controlled pore glass (CPG) membrane. One or more DNA wash solutions can be added through inlet 138 to wash out contaminants and impurities that may negatively affect sequencing. Wash solutions for DNA purification are well known to those of ordinary skill in the art and may include solutions of chaotropic salts and/or ethanol. The wash solution(s) may remove remnants of calcium alginate shells. The wash solution(s) may flow through outlet 140 to a waste collection system. After washing an elution reagent is flowed from inlet 138 through the membrane 136 to release the DNA. The elution reagent may be an elution buffer or unbuffered water such as molecular water or distilled water. Elution buffers for DNA purification are well known to those of ordinary skill in the art and may include, for example, 10 mM Tris at pH 8-9, TE buffer containing 10 mM Tris and 1 mM EDTA.

After the DNA is cleaned, the system 100 may include a component for selecting DNA by size (not shown). PCR may create side products which will typically have different lengths than the desired amplification products. A size-selection step may be used to separate the desired amplification products from the side products. Size selection may be performed by gel or capillary electrophoresis. Techniques for performing gel or capillary electrophoresis of DNA are well known to those of ordinary skill in the art.

The DNA released from the membrane 136 flows out of the system 100 through outlet 142 where the DNA may be stored or sent to a DNA sequencer such as a multiplex DNA sequencer. The DNA may be stored for a relatively short time in an aqueous solution such as the elution buffer. The DNA may be stored for a relatively longer period of time as a lyophilized pellet, encased in a protective coating, dried onto filter paper, or by another technique that preserves the structure of the DNA.

The outflow from outlet 142 contains amplification products in response to multiple different random-access requests but the amplification products are copy-normalized DNA in which every DNA strand amplified by PCR is present in about the same number of copies. Thus, approximately equal quantities of DNA are provided to the DNA sequencer in response to each random-access request. This improves efficiency and accuracy of multiplex sequencing.

Figure 2:
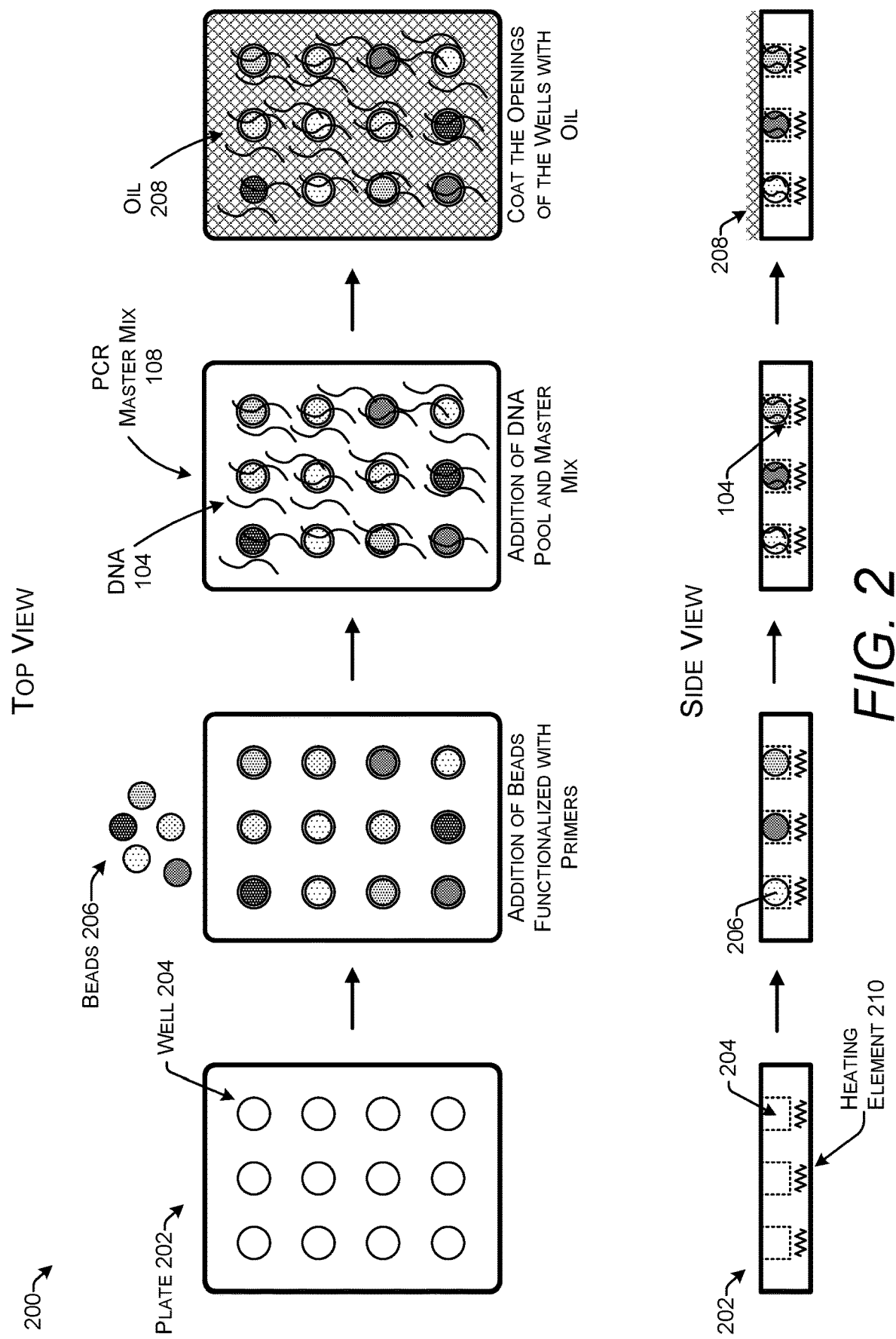
FIG. 2 is a diagram of an illustrative system for generating samples of DNA in wells with beads that provide a primer pair as bound oligonucleotides.

FIG. 2 shows a second illustrative random-access system 200 for that uses a plate 202 with a plurality of wells 204 to generate PCR amplification products with normalized quantities of DNA. In this illustration, the plate 202 contains 12 wells; however, in practice the plate 202 may include any number of wells and will typically include many more such as, for example, 1536 wells. The plate 202 is formed out of insulating material that inhibits heat transfer between the wells 204. In one implementation, plate 202 may be formed from silicon dioxide. Creation of the plate 202 and the wells 204 may be performed using techniques adapted from semiconductor fabrication. Creating the plate 202 semiconductor chip allows for creation of nanometer-scale structures such as wells with diameters in the range of single micrometers.

Immobilized primer pairs are provided on beads 206. The beads 206 may be, for example, amino-silanized CPG beads. The primer pairs are anchored to the beads either directly or via linkers. With both primers immobilized, PCR proceeds with bridge amplification similar to the technique used in sequencing-by-synthesis. Example techniques for performing PCR with primers immobilized on beads are provided in Joanne D. Andreadis & Linda A. Chrisey, *Use of Immobilized PCR Primers to Generate Covalently Immobilized DNAs for In Vitro Transcription/Translation Reactions*, 28 (2) Nuc. Acids Res. e5(i) (2000).

In an implementation, the beads 206 and the wells 204 may be sized such that one and only one bead 206 can fit into each well. Thus, by flowing the beads 206 over the surface of the plate 202 each well 204 will be filled with a single primer pair 106. Some wells 204 may remain empty depending on the quantity of beads 206 and the technique used to provide the beads to the well 204. It may also be unknown which bead 206 occupies which well 204.

The DNA 104 from a single DNA pool and the PCR master mix 108 may be added to all the wells 204 in the plate 202. Because in some implementations a single aqueous solution is flowed into all of the wells 204, the DNA 104 may be limited to DNA from only a single DNA pool. At this point, many or all of the wells 204 contains a single primer pair 106, DNA 104 and the PCR master mix 108.

The surface of the plate 202 may be coated with an oil 208 such as mineral oil. The oil 208 may contain surfactants (e.g., Tween 80 or Abil® Em 90). The oil 208 forms a coating over the openings of the wells 204 creating isolated reaction volumes in each well 204.

The thermocycling necessary for PCR may be performed by heating the entire plate 202 in a thermocycler. In some implementations, the heating of each individual well 204 may be controlled separately. For example, the plate 202 may be fabricated such that there is a separately-addressable heating element 210 (e.g. a resistor) underneath some or all of the wells 204. The heating element 210 is able to raise the temperature of the well 204 underneath which it is situated without significantly affecting the temperature of any adjacent wells 204. The entire plate 202 may be cooled by exposure to air (e.g., by use of a heat sink), cooled fluids, or by use of a heat pump. In some implementations, the plate 202 may be fabricated with a Peltier device underneath each well 204. These Peltier devices function as the separately-addressable heating elements 210 and also cool the wells 204 in order to provide the temperature changes needed for PCR.

PCR is performed in the wells 204 and the quantity of DNA generated in each well 204 may be measured using any suitable technique such as by detecting fluorescence of an intercalating dye. The quantity of DNA in each well 204 may vary due to differences in the amplification efficiency of the primer pairs. The quantity of DNA may be detected in real time as PCR proceeds.

If the wells 204 are equipped with separately-addressable heating elements 210, additional PCR cycles may be added selectively to those wells 204 with low quantities of DNA. For example, any wells 204 for which the quantity of DNA is determined to be less than a threshold value may receive additional cycles of PCR. PCR may be continued in those wells with lower quantities of DNA until all the wells 204 in the plate 202 have approximate the same quantity of DNA.

For example, after a standard cycle of PCR amplification the quantity of DNA in the well 204 with the highest quantity of DNA may be set as the threshold. No further PCR is performed for the wells 204 with this quantity of DNA. However, for all the wells 204 with lower quantities of DNA (e.g., as detected by lower fluorescence levels) PCR is continued either for a set number of cycles or until real-time detection indicates that the quantity of DNA is the same or approximately the same as the threshold. The ability to separate the control number PCR amplification cycles for individual wells 204 makes it possible to provide copy-normalize DNA quantities in all of the wells 204 in a given plate 202.

The contents of the wells 204 can be combined after normalization and analyzed using multiplex sequencing. The beads 206 may be discarded or cleaned and reused. After PCR the amplification products in the wells 204 may be cleaned and/or sorted by size using any of the techniques discussed above in association with system 100 shown in FIG. 1.

Figure 3:
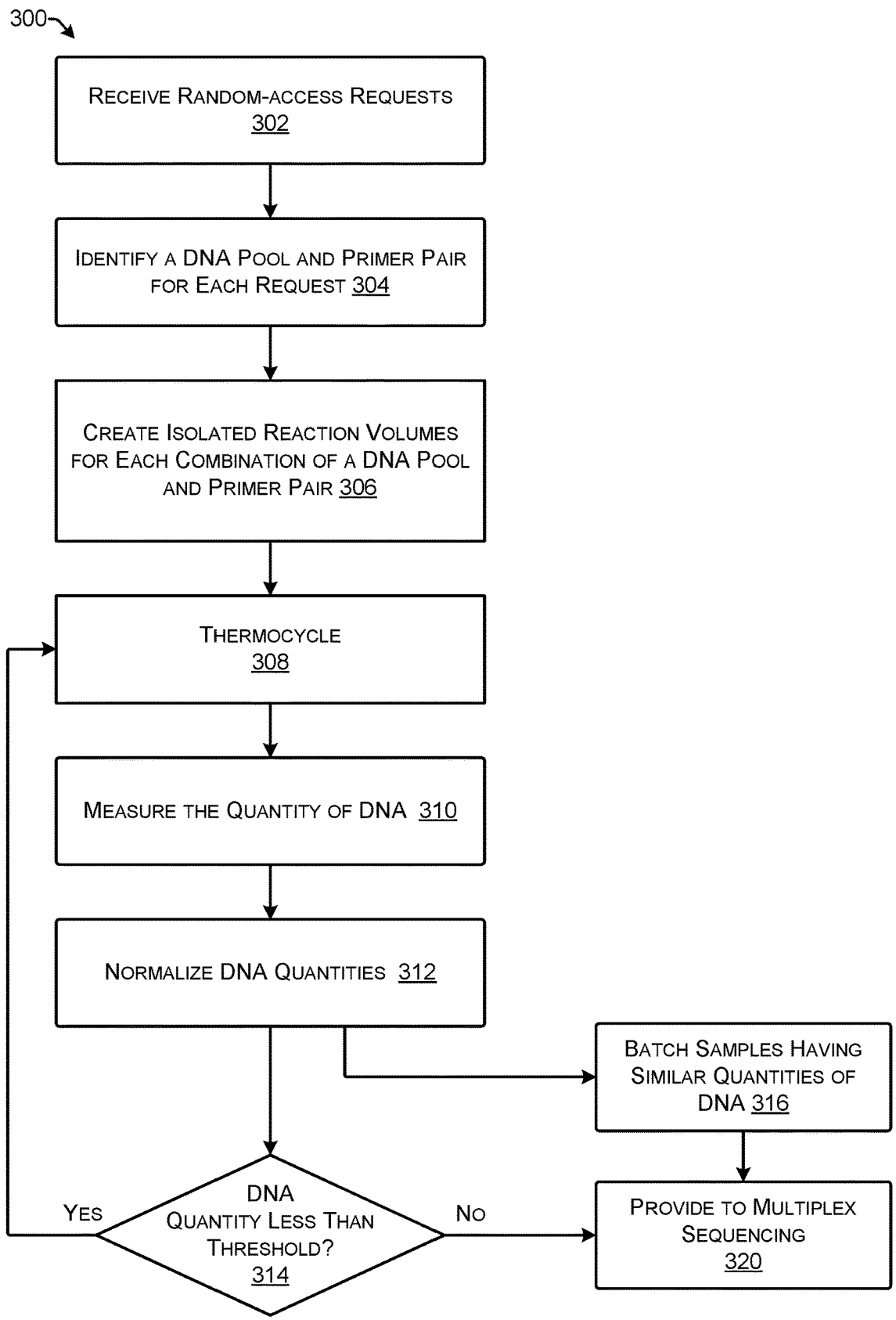
FIG. 3 is a flow diagram showing an illustrative process for generating samples of DNA with normalized DNA quantities for multiplex sequencing.

FIG. 3 shows process 300 for generating samples of DNA with copy-normalized DNA quantities for multiplex sequencing. This process 300 may be implemented, for example, using either of the systems shown in FIGS. 1 and 2.

At operation 302, one or more random-access requests are received. The random-access requests may be received by one or more computer systems that manages a DNA data storage system. The random-access requests may be requests for specific sets of digital data such as specific computer files.

At operation 304, a DNA pool and primer pair are identified for each request. If there are multiple requests one or more DNA pools and multiple primer pairs may be identified in response to those random-access queries. The DNA data storage system contains strands of DNA organized into one or more DNA pools. Each strand of DNA is synthetically created according to a schema that includes both a payload region and flanking primer binding sites. Amplification with PCR primers that hybridize to the primer binding sites creates many copies of the payload region which can then be sequenced and decoded to obtain the digital data specified in the random-access request. The digital data is correlated to a specific DNA pool and primer pair by the computer systems (e.g., by using a lookup table).

At operation 306, a plurality of isolated reaction volumes are created. Each of the isolated reaction volumes comprises a portion of one of the DNA pools, a primer pair, and PCR master mix. The PCR master mix may also contain a dye such as an intercalating fluorescent dye. The number of isolated reaction volumes created may depend on the number of random-access requests received at 302. In an implementation, there is one isolated reaction volume created for each random-access request. Thus, each isolated reaction volume will contain a unique combination of a portion of DNA from a DNA pool and a primer pair. In other implementations, multiple isolated reaction volumes that contain the same combination of DNA and primer pair may be created either intentionally or unintentionally.

The isolated reaction volumes may be formed as microdroplets such as a water-in-oil emulsion or as a calcium alginate emulsion. Water-in-oil emulsions may be formed using a T-junction as described above.

Isolated reaction volumes may alternatively be formed as wells in a plate. The primer pairs may be provided by functionalizing each of the plurality of beads with a single primer pair. The plurality of beads are placed into a plurality of wells in a plate. The size and shape of the beads in the wells may be such that each of the plurality of wells is sized to hold at most a single one of the plurality of beads. This provides a single, unique primer pair to each isolated reaction volume.

At operation 308, the plurality of isolated reaction volumes are thermocycled under conditions suitable for PCR. Persons of ordinary skill in the art will readily understand how to perform PCR including selection of a specific series of temperature changes and number of cycles.

At operation 310, the quantity of DNA is measured in some or all of the plurality of isolated reaction volumes. Any suitable technique for measuring DNA may be used. For example, the quantity of DNA may be measured by measuring the fluorescence of a dye such as an intercalating fluorescent dye.

At operation 312, the quantity of DNA in a selection of the isolated reaction volumes is normalized prior to multiplex sequencing. The selection of isolated reaction volumes may, in some implementations, include all of the isolated reaction volumes such as all of the microdroplets or all of the wells. Copy-normalization may be performed by performing additional PCR cycles or by batching samples with similar quantities of DNA.

If copy-normalization is performed by additional PCR cycles, process 300 proceeds to operation 314 where it is determined if the quantity of DNA in individual ones of the isolated reaction volumes is less than a threshold value. The quantity of DNA may be determined and compared to a threshold value for each of the isolated reaction volumes. The threshold value may be predetermined based on previous experience. The threshold value may be derived from a measured value of the individual ones of the isolated reaction volumes. For example, the threshold value may be the quantity of DNA in the one of the plurality of isolated reaction volumes that has the highest quality of DNA. As a further example, the threshold value may be defined relative to the quantity of DNA in the one of the plurality of isolated reaction volumes that has the highest quantity of DNA (e.g. example 80%, 90%, 95%, of the highest quantity).

For an individual one of the isolated reaction volumes, if the quantity of DNA is not less than the threshold value, process 300 proceeds from operation 314 to operation 316. If, however, the quantity of DNA is less than the threshold value, process 300 proceeds from operation 314 back to operation 308 where thermocycling is continued. The thermocycling may be continued by returning individual microdroplets to a reaction chamber where they are subject to further rounds of heating and cooling to continue the PCR. The thermocycling may be continued for DNA in wells of a plate by providing additional heating and cooling cycles to those wells without performing the same heating and cooling on the entire plate.

If copy-normalization is provided by batching, process 300 proceeds from operation 312 to operation 318. At operation 318, individual ones of the plurality of isolated reaction volumes that have a quantity of DNA within a range of values are batched into the same multiplex sequencing run. The values used for the range of values may be defined in advance or based on measured DNA quantities. Two ranges of values (e.g., from 0 to a threshold and from the threshold to infinity) may be used to batch the isolated reaction volumes into two batches. Similarly, a larger number of ranges may be used to divide the isolated reaction volumes into three or more different batches. Batching may be performed, for example, by using microfluidics and/or cell-sorting techniques such as electrostatic sorting.

At operation 320, the copy-normalized amplification products are provided to a multiplex DNA sequencer. All of the DNA from each of the isolated reaction volumes is mixed together when provided to the multiplex DNA sequencer. Because the quantity of DNA from each of the isolated reaction volumes, which correspond to separate random-access requests, is normalized (i.e., the same or approximately the same) the DNA strands corresponding to each random-access request are represented approximately equally in the flow cell of the multiplex DNA sequencer.

The multiplex DNA sequencer generates output strings which represent the order of nucleotide bases in the DNA strands present in the flow cell. The strength of the signals generated by reading the DNA corresponding to the random-access requests are approximately equal because of copy-normalization, so the multiplex DNA sequencer is able to generate sequence output in which there is approximately equal depth of coverage for each sample. This creates accurate sequence output without consuming necessary reagents or using bandwidth of the multiplex DNA sequencer to generate additional, unnecessary coverage depth.

Pre-Calibration Based on Primer Efficiency

The techniques discussed above are based on measured quantities of DNA in individual reaction volumes. As mentioned earlier, one source of variation for the quantities of DNA created by PCR amplification is variations in primer efficiency. Some features of primer efficiency may be identified, or at least estimated, based only on the sequence of nucleotides in a primer pair. Thus, it is possible to preemptively modify aspects of the random-access techniques and systems discussed above based on knowledge of the relative efficiency of the primer pairs being used to respond to a plurality of random-access requests.

Primer efficiency is related to amplification efficiency. If the quantity of DNA doubles during each cycle of a PCR reaction than amplification efficiency is 100%. Primer efficiency values may also be represented as a percentage based on the effect a given primer pair has on amplification efficiency. Thus, if amplification efficiency is 100% with a highly efficient primer pair but under the same conditions amplification efficiency is only 90% with a different primer pair, then this different primer pair is said to have 90% primer efficiency value. Persons of ordinary skill in the art are aware of techniques for calculating primer efficiency values such as by creation of a standard curve. Some commercially available thermocyclers are also able to automatically calculate primer efficiency values.

Primer efficiency values may be identified for each primer pair that can be used to query a DNA pool. Because of the design of the DNA molecules placed into each DNA pool, the primer pairs used in response to random-access requests are known. Once primer efficiency values are available for each of the primer pairs, they may be stored in electronic format such as in a table, database, etc.

One way that primer efficiency may be used is by identifying a primer efficiency value for a particular primer pair and then adjusting the number of isolated reaction volumes that contain the particular primer pair based on the primer efficiency value. The number of individual, reaction volumes created for a random-access request may be inversely proportional to the primer efficiency value of the primer pair. As the primer efficiency decreases a greater number of isolated reaction volumes are created with that primer pair.

The number of microdroplets containing a particular primer pair may be adjusted based on the primer efficiency value. More microdroplets containing a low-efficiency primer pair can be created. Thus, some combinations of DNA and primer pairs may be present in only a single microdroplet, but others may be present in two, three, or more microdroplets. When the primer pair is provided on a bead, the number of beads functionalized with a particular primer pairs may be adjusted based on the primer efficiency value. The number of beads that have primer pairs with low primer efficiency values may be increased so that there may be two, three, or more wells in a plate filled with beads coated with the same primer pair. Although the quantity of DNA in each isolated reaction volume is not changed, there are more isolated reaction volumes containing the same amplification products which are combined prior to sequencing thereby increasing the total quantity of DNA provided to a DNA sequencer.

Wells filled with beads that provide low-efficiency primer pairs may be subject to additional rounds of thermocycling (possibly absent any measurement of DNA quantity) so that the final quantity of amplification products is similar to that of other wells. There are multiple possible techniques to identify which wells contain a specific bead. Individual beads may be placed into specific wells using microfluidics and laboratory robotics and the location recorded. Beads that are functionalized with low-efficiency primer pairs may also be marked either by functionalization with other molecules that are identifiable (e.g. dyes, radioactive tags, etc.) or the bead itself may be different (e.g., in color, radioactivity, quantity of ferromagnetic material, etc.). Those wells containing the beads functionalized with low-efficiency primer pairs may receive additional cycles of PCR in inverse proportion to the primer efficiency (i.e., the lower the efficiency the greater the number of PCR cycles).

Another technique for adjusting processing based on primer efficiency values includes adjusting the relative concentrations or amounts of the components of the PCR reaction. The relative concentrations may be changed by increasing or decreasing the amount of any or all of the components of the PCR reaction. The quantity of DNA may be adjusted by changing the quantity of DNA drawn from the DNA pool used (e.g., a larger quantity of DNA may be used with low-efficiency primer pairs). The quantity of DNA drawn from the pool may be adjusted by taking a larger or smaller volume of sample from the DNA pool. If the volume of the sample is changed, the volume of another component (e.g., a buffer) may be increased or decreased by an equal amount to maintain a constant volume. Alternatively, if the sample drawn from the DNA pool is diluted prior to mixing with other reagents, the extent of the dilution may be changed in order to obtain a greater lesser quantity of DNA. The quantity of the primer pair itself may be adjusted by providing more or fewer molecules of the primers (e.g., the quantity of each primer in the primer pair may be increased in inverse proportion to the primer efficiency). Additionally, the concentration of the PCR master mix may be changed based on the primer efficiency values.

Illustrative Computer Architecture

Figure 4:
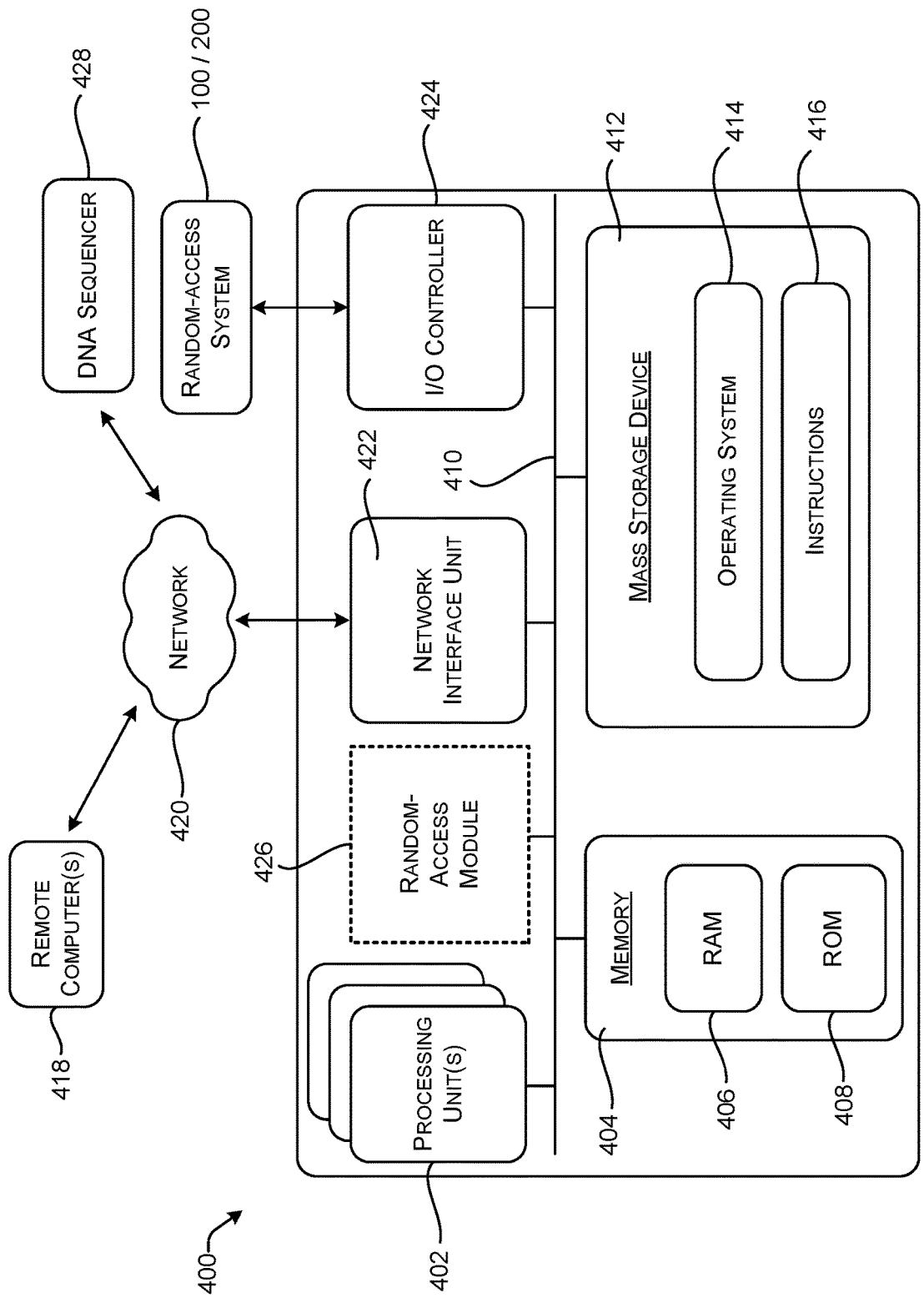
FIG. 4 is an illustrative computer system and architecture for implementing techniques of this disclosure.

FIG. 4 is a computer architecture diagram showing an illustrative computer hardware and software architecture for a computing device. In particular, the computer 400 illustrated in FIG. 6 can be used to control either of the random-access systems 100, 200 shown in FIGS. 1 and 2 as well as to control a DNA sequencer 428.

The computer 400 includes one or more processing units 402, a memory 404, that may include a random-access memory 406 ("RAM") and a read-only memory ("ROM") 408, and a system bus 410 that couples the memory 404 to the processing unit(s) 402. A basic input/output system ("BIOS" or "firmware") containing the basic routines that help to transfer information between elements within the computer 400, such as during startup, can be stored in the ROM 408. The computer 400 further includes a mass storage device 412 for storing an operating system 414 and other instructions 416 that represent amplification programs and/or other types of programs such as, for example, instructions to implement the random-access module 426. The mass storage device 412 can also be configured to store files, documents, and data such as, for example, sequence data that is obtained from a DNA sequencer 428.

The mass storage device 412 is connected to the processing unit(s) 402 through a mass storage controller (not shown) connected to the bus 410. The mass storage device 412 and its associated computer-readable media provide non-volatile storage for the computer 400. Although the description of computer-readable media contained herein refers to a mass storage device, such as a hard disk, solid-state drive, CD-ROM drive, DVD-ROM drive, or USB storage key, it should be appreciated by those skilled in the art that computer-readable media can be any available computer-readable storage media or communication media that can be accessed by the computer 400.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules or other data. For example, computer-readable storage media includes, but is not limited to, RAM 406, ROM 408, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 400. For purposes of the claims, the phrase "computer-readable storage medium," and variations thereof, does not include waves or signals per se or communication media.

According to various configurations, the computer 400 can operate in a networked environment using logical connections to a remote computer(s) 418 through a network 420. The computer 400 can connect to the network 420 through a network interface unit 422 connected to the bus 410. It should be appreciated that the network interface unit 422 can also be utilized to connect to other types of networks and remote computer systems. The computer 400 can also include an input/output (I/O) controller 424 for receiving and processing input from a number of other devices, including a keyboard, mouse, touch input, an electronic stylus (not shown), or equipment such as a DNA sequencer 428 and/or a random-access system 100, 200. Similarly, the input/output controller 424 can provide output to a display screen or other type of output device (not shown).

It should be appreciated that the software components described herein, when loaded into the processing unit(s) 402 and executed, can transform the processing unit(s) 402 and the overall computer 400 from a general-purpose computing device into a special-purpose computing device customized to facilitate the functionality presented herein. The processing unit(s) 402 can be constructed from any number of transistors or other discrete circuit elements, which can individually or collectively assume any number of states. More specifically, the processing unit(s) 402 can operate as a finite-state machine, in response to executable instructions contained within the software modules disclosed herein. These computer-executable instructions can transform the processing unit(s) 402 by specifying how the processing unit(s) 402 transitions between states, thereby transforming the transistors or other discrete hardware elements constituting the processing unit(s) 402.

Encoding the software modules presented herein can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 400 to store and execute the software components presented herein. It also should be appreciated that the architecture shown in FIG. 4 for the computer 400, or a similar architecture, can be utilized to implement many types of computing devices such as desktop computers, notebook computers, servers, supercomputers, gaming devices, tablet computers, and other types of computing devices known to those skilled in the art. For example, the computer 400 may be wholly or partially integrated into one or both of the DNA sequencer 428 and the random-access system 100, 200. It is also contemplated that the computer 400 might not include all of the components shown in FIG. 4, can include other components that are not explicitly shown in FIG. 4, or can utilize an architecture different than that shown in FIG. 4.

The computer 400 may include a random-access module 426 that can control formulation of the inputs to a random-access system 100, 200 and additionally control operation of the random-access system 100, 200 itself. For example, random-access requests for digital data received by the computer 400 may be translated into a DNA pool and primer pair by the random-access module 426. As mentioned above, this translation may be performed by using a look-up table or other record of correlation. The random-access module 426 may also generate instructions to control microfluidic devices (e.g., Puddle) and/or laboratory robotics. The random-access module 426 may further control modifications to random-access protocols based on primer efficiency values.

The DNA sequencer 428 may be any conventional or later-developed type of DNA sequencing technique. Common sequencing techniques include dideoxy sequencing reactions, NGS, and nanopore sequencing. Classic dideoxy sequencing reactions (Sanger method) use labeled terminators or primers and gel separation in slab or capillary electrophoresis.

NGS refers to any of a number of post-classic Sanger type sequencing methods which are capable of high throughput, multiplex sequencing of large numbers of samples simultaneously. Current NGS sequencing platforms are capable of generating reads from multiple distinct nucleic acids in the same sequencing run.

Nanopore sequencing uses a small hole, a "nanopore," on the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of preparing copy-normalized oligonucleotide samples for multiplex sequencing comprising: identifying one or more oligonucleotide pools and multiple primer pairs responsive to random-access request; creating a plurality of isolated reaction volumes each comprising a portion of a one of the oligonucleotide pools, a primer pair, and polymerase chain reaction (PCR) master mix; thermocycling the plurality of isolated reaction volumes under conditions suitable for PCR; measuring a quantity of oligonucleotides in individual ones of the plurality of isolated reaction volumes; and normalizing the quantity of oligonucleotides in a selection of the plurality of isolated reaction volumes prior to multiplex sequencing.

Clause 2. The method of clause 1, wherein the isolated reaction volumes are microdroplets.

Clause 3. The method of clause 1, wherein the isolated reaction volumes are wells containing beads functionalized with one of the multiple primer pairs.

Clause 4. The method of any of clauses 1-3, wherein the measuring the quantity of oligonucleotides comprises measuring fluorescence of a fluorescent dye.

Clause 5. The method of any of clauses 1-4, wherein normalizing the quantity of oligonucleotides comprises batching individual ones of the plurality of isolated reaction volumes having a quantity of oligonucleotides within a range of values into a same multiplex sequencing run.

Clause 6. The method of any of clauses 1-4, wherein normalizing the quantity of oligonucleotides comprises continuing thermocycling of individual ones of the plurality of isolated reaction volumes for which the quantity of oligonucleotides is less than a threshold value.

Clause 7. The method of any of clauses 1-6, further comprising: identifying a primer efficiency value for a particular primer pair; and based on the primer efficiency value adjusting (i) a number of the isolated reaction volumes that contain the particular primer pair; or (ii) a relative concentration of at least one of the portions of the one of the oligonucleotide pools, the primer pair, or the PCR master mix.

Clause 8. A method of preparing copy-normalized oligonucleotide samples for multiplex sequencing comprising: forming a plurality of microdroplets each containing a portion of an oligonucleotide pool, a primer pair, and polymerase chain reaction (PCR) master mix; thermocycling the plurality of microdroplets under conditions suitable for PCR; measuring a quantity of oligonucleotides in individual ones of the plurality of microdroplets; and normalizing the quantity of oligonucleotides in a selection of the plurality of microdroplets prior to multiplex sequencing.

Clause 9. The method of clause 8, wherein the microdroplets are formed by a water-in-oil emulsion.

Clause 10. The method of clause 8, wherein the microdroplets are formed by a calcium alginate emulsion.

Clause 11. The method of any of clauses 8-10, wherein measuring the quantity of oligonucleotides comprises measuring fluorescence of a fluorescent dye.

Clause 12. The method of any of clauses 8-11, wherein normalizing the quantity of oligonucleotides comprises batching individual ones of the plurality of microdroplets having a quantity of oligonucleotides within a range of values into a same multiplex sequencing run.

Clause 13. The method of any of clauses 8-11, wherein normalizing the quantity of oligonucleotides comprises continuing thermocycling of individual ones of the plurality of microdroplets for which the quantity of oligonucleotides is less than a threshold value.

Clause 14. The method of any of clauses 8-13, further comprising: identifying a primer efficiency value for a particular primer pair; and based on the primer efficiency value adjusting (i) a number of microdroplets formed that contain the particular primer pair or (ii) a relative concentration of at least one of the portion of the one of the oligonucleotide pools, the primer pair, or the PCR master mix.

Clause 15. A method of preparing copy-normalized oligonucleotide samples for multiplex sequencing comprising: functionalizing each of a plurality of beads with a primer pair; placing the plurality of beads into a plurality of wells, wherein each well of the plurality of wells is sized to hold at most a single one of the plurality of beads; contacting the plurality of wells with a portion of a pool of oligonucleotides and a polymerase chain reaction (PCR) master mix; thermocycling contents of the wells under conditions suitable for PCR; measuring a quantity of oligonucleotides in individual ones of the plurality of wells; determining that the quantity of oligonucleotides in one of the plurality of wells is less than a threshold value; and thermocycling the contents of the one of the plurality of wells.

Clause 16. The method of clause 15, wherein measuring the quantity of oligonucleotides comprises measuring fluorescence of a fluorescent dye.

Clause 17. The method of any of clauses 15-16, wherein the plurality of wells are wells in a plate and the plate comprises separately-addressable heating elements located beneath the plurality of wells.

Clause 18. The method of any of clauses 15-17, further comprising coating openings of the wells with oil.

Clause 19. The method of any of clauses 15-18, further comprising: identifying a primer efficiency value for a particular primer pair; and based on the primer efficiency value (i) adjusting a number of beads functionalized with the particular primer pair that are placed into the plurality of wells or (ii) adding an additional portion of the pool of oligonucleotides or additional PCR master mix to the plurality of wells.

Clause 20. The method of any of clauses 15-19, further comprising: combining oligonucleotides from the plurality of wells; and providing the combined oligonucleotides for multiplex sequencing.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents, and/or patent applications throughout this specification. Each of the cited references is individually incorporated herein by reference for its particular cited teachings as well as for all that it discloses.

The invention claimed is:

1. A method of preparing copy-normalized oligonucleotide samples for multiplex sequencing comprising:
identifying one or more oligonucleotide pools and multiple primer pairs responsive to multiple random-access requests, wherein each random-access request corresponds to a different primer pair;
creating a plurality of isolated reaction volumes each comprising a portion of one of the oligonucleotide pools, one of the multiple primer pairs, and polymerase chain reaction (PCR) master mix;

thermocycling the plurality of isolated reaction volumes under conditions suitable for PCR;

measuring a quantity of oligonucleotides in individual ones of the plurality of isolated reaction volumes; and normalizing the quantity of oligonucleotides in a selection of the plurality of isolated reaction volumes prior to multiplex sequencing.

2. The method of claim 1, wherein the isolated reaction volumes are microdroplets.

3. The method of claim 1, wherein the isolated reaction volumes are wells containing beads functionalized with one of the multiple primer pairs.

4. The method of claim 1, wherein the measuring the quantity of oligonucleotides comprises measuring fluorescence of a fluorescent dye.

5. The method of claim 1, wherein normalizing the quantity of oligonucleotides comprises batching individual ones of the plurality of isolated reaction volumes having a quantity of oligonucleotides within a range of values into a same multiplex sequencing run.

6. The method of claim 1, wherein normalizing the quantity of oligonucleotides comprises continuing thermocycling of individual ones of the plurality of isolated reaction volumes for which the quantity of oligonucleotides is less than a threshold value.

7. The method of claim 1, further comprising:
identifying a primer efficiency value for a particular primer pair; and
based on the primer efficiency value adjusting (i) a number of the isolated reaction volumes that contain the particular primer pair; or (ii) a relative concentration of at least one of the portions of the one of the oligonucleotide pools, the primer pair, or the PCR master mix.

8. A method of preparing copy-normalized oligonucleotide samples for multiplex sequencing comprising:
forming a plurality of microdroplets each containing a portion of an oligonucleotide pool, a primer pair, and polymerase chain reaction (PCR) master mix;
thermocycling the plurality of microdroplets under conditions suitable for PCR;
measuring a quantity of oligonucleotides in individual ones of the plurality of microdroplets; and
normalizing the quantity of oligonucleotides in a selection of the plurality of microdroplets prior to multiplex sequencing, wherein normalizing the quantity of oligonucleotides comprises batching individual ones of the plurality of microdroplets having a quantity of oligonucleotides within a range of values into a same multiplex sequencing run.

9. The method of claim 8, wherein the microdroplets are formed by a water-in-oil emulsion.

10. The method of claim 8, wherein the microdroplets are formed by a calcium alginate emulsion.

11. The method of claim 8, wherein measuring the quantity of oligonucleotides comprises measuring fluorescence of a fluorescent dye.

12. The method of claim 8, further comprising:
identifying a primer efficiency value for a particular primer pair; and
based on the primer efficiency value adjusting (i) a number of microdroplets formed that contain the particular primer pair or (ii) a relative concentration of at least one of the portions of the oligonucleotide pool, the primer pair, or the PCR master mix.

13. A method of preparing copy-normalized oligonucleotide samples for multiplex sequencing comprising:
forming a plurality of microdroplets each containing a portion of an oligonucleotide pool, one of multiple different primer pairs, and polymerase chain reaction (PCR) master mix, wherein a first portion of the plurality of microdroplets contains a first primer pair and a second portion of the plurality of microdroplets contains a second primer pair;
thermocycling the plurality of microdroplets under conditions suitable for PCR;
measuring a quantity of oligonucleotides in individual ones of the plurality of microdroplets; and
normalizing the quantity of oligonucleotides in a selection of the plurality of microdroplets prior to multiplex sequencing.

14. The method of claim 13, wherein the microdroplets are formed by a water-in-oil emulsion.

15. The method of claim 13, wherein the microdroplets are formed by a calcium alginate emulsion.

16. The method of claim 13, wherein measuring the quantity of oligonucleotides comprises measuring fluorescence of a fluorescent dye.

17. The method of claim 13, wherein normalizing the quantity of oligonucleotides comprises batching individual ones of the plurality of microdroplets having a quantity of oligonucleotides within a range of values into a same multiplex sequencing run.

18. The method of claim 13, wherein normalizing the quantity of oligonucleotides comprises continuing thermocycling of individual ones of the plurality of microdroplets for which the quantity of oligonucleotides is less than a threshold value.

19. The method of claim 13, further comprising:
identifying a primer efficiency value for a particular primer pair; and
based on the primer efficiency value adjusting (i) a number of microdroplets formed that contain the particular primer pair or (ii) a relative concentration of at least one of the portions of the oligonucleotide pool, the primer pair, or the PCR master mix.

* * * * *